United States Patent [19]

Harada et al.

[11] Patent Number: 4,918,206

[45] Date of Patent: Apr. 17, 1990

[54] SULFAMOYL-2-BENZOFURANCARBOXYLIC ACID DERIVATIVE

[75] Inventors: Hiroshi Harada; Yoshihiro Matsushita; Masuhisa Nakamura, all of Osaka; Yukio Yonetani, Nara, all of Japan

[73] Assignee: Shionogi & Co., Ltd., Osaka, Japan

[21] Appl. No.: 245,294

[22] Filed: Sep. 16, 1988

[30] Foreign Application Priority Data

Oct. 12, 1987 [JP] Japan ................................ 62-256890

[51] Int. Cl.$^4$ ............................................ C07D 307/85
[52] U.S. Cl. .................................... 549/468; 544/153; 546/196; 548/525

[58] Field of Search ...................... 549/468; 544/153; 546/196; 548/525

[56] References Cited

U.S. PATENT DOCUMENTS

| 4,659,709 | 4/1987 | Harada et al. | ....................... 549/468 |
| 4,663,347 | 5/1987 | Atkinson et al. | ................... 549/468 |

Primary Examiner—Mary C. Lee
Assistant Examiner—Bernard I. Dentz
Attorney, Agent, or Firm—Wenderoth, Lind & Ponack

[57] ABSTRACT

Highly effective diuretic antihypertensives, i.e., sulfamoyl-2-benzofurancarboxylic acid derivatives which are classified as loop diuretics with less adverse side-effects and can be administered orally at a daily dosage of 0.5 mg to 200 mg or parenterally at 0.01 mg to 50 mg.

7 Claims, No Drawings

SULFAMOYL-2-BENZOFURANCARBOXYLIC ACID DERIVATIVE

BACKGROUND OF THE INVENTION

1. Field of the Invention

The present invention relates to novel compounds with antihypertensive and diuretic activities, namely, sulfamoyl-2-benzofurancarboxylic acid derivatives. The compounds which the present invention provides are very promising as diuretic antihypertensives.

2. Prior Art 2,3-Dihydrobenzofuran-5-sulfonamide derivatives are disclosed in KOKAI 61-63671 as useful uricosuric antihypertensives.

It has been known that 2,3-dihydrobenzofuran compounds have potent uricosuric and saluretic activities. They are racemates because of the asymmetric carbon atom at the 2-position. It becomes known from recent studies that one of the enantiomers has a uricosuric activity rather than saluretic activity in comparison with the other or vice versa. A racemate resolution method, by which the objective compounds are resolved in the final stage, is disclosed in J. Med. Chem. 24, 865–873 (1981) and another method is disclosed in Japanese Patent Application No. 61-248121, by which ($\pm$)-6,7-dichloro-2,3-dihydrobenzofuran-2-carboxylic acid of the formula:

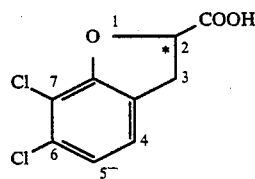

that is an important intermediate for those compounds, is resolved.

SUMMARY OF THE INVENTION

The present invention provides very useful diuretic antihypertensives, sulfamoyl-2-benzofurancarboxylic acid derivatives represented by the following formula (A):

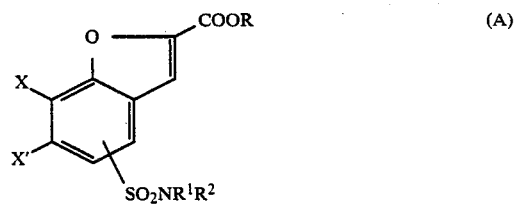

wherein R is hydrogen or a protecting group; $R^1$ and $R^2$ are the same or different and each is hydrogen, lower alkyl, 4- to 7-membered cycloalkyl, optionally substituted phenyl, phenyl-lower alkyl, lower alkoxycarbonyl, or morpholino-lower alkyl or $R^1$ and $R^2$ may form an optionally substituted 5- or 6-membered heterocycle, together with the adjacent nitrogen atom, which may have one or more additional hetero atoms; and X and X' each is hydrogen or halogen.

DESCRIPTION OF THE PREFERRED EMBODIMENT

As mentioned above, most of 2,3-dihydrobenzofuran compounds are racemates and each enantiomer has either a diuretic activity or a uricosuric activity. However, if only either diuretics or uricosurics are intended to be developed, an objective enantiomer should be isolated through racemic resolution as aforementioned. This strongly affects the production costs because another enantiomer is unnecessarily produced.

The compounds which the present invention provides have no asymmetric carbon atom in the molecule and, therefore, are nonracemic. Since each of them has potent saluretic activity with substantially no uricosuric activity, a serial of diuretics can be economically developed because of less loss in production.

The compounds (A) as shown above can, by the properties of the substituents thereof, be acid addition salts or the salts with an alkali metal, alkaline earth metal, organic base or the like. The acid addition salts include, for example, salts with hydrochloric acid, hydrobromic acid, nitric acid, sulfuric acid, phosphoric acid, perchloric acid, oxalic acid, malonic acid, succinic acid, malic acid, lactic acid, or the like. The salts with a metal or an organic base include, for example, salts with sodium, potassium, calcium, magnesium, triethylamine, dimethylaniline, N-methylmorpholine, amyloride, or the like.

The lower alkyl indicated by $R^1$ or $R^2$ means straight or branched chain $C_1$–$C_5$ alkyl such as methyl, ethyl, propyl, isopropyl, butyl, s-butyl, isobutyl, pentyl, isopentyl, and the like.

Four- to seven-membered cycloalkyl is cyclobutyl, cyclopentyl, cyclohexyl, or cycloheptyl.

The optionally substituted phenyl, whose substituent is halo such as fluoro, chloro, and bromo; alkoxy such as methoxy, ethoxy; or the like, includes p-methoxyphenyl, p-chlorophenyl, or the like.

Phenyl-lower alkyl, which means the above-identified lower alkyl substituted by phenyl, includes benzyl, phenethyl, phenylpropyl, and the like.

The lower alkoxycarbonyl, which means an alkoxycarbonyl formed by oxycarbonyl and the above-identified lower alkyl, includes methoxycarbonyl, ethoxycarbonyl, propoxycarbonyl, butoxycarbonyl, and the like.

Morpholino-lower alkyl means an above-identified lower alkyl which is substituted by morpholino and includes morpholinomethyl, morpholinoethyl, morpholinopropyl and the like.

The optionally substituted 5- or 6-membered heterocycle, which is formed by $R^1$ and $R^2$ together with the adjacent nitrogen atom and may have one or more additional hetero atoms, is represented by pyrrolidino, piperidino, morpholino, or the like, wherein the substituent is a lower alkyl.

Halogen indicated by X and X' includes fluoro, chloro, or bromo, wherein chloro is especially preferred.

The protecting group indicated by R includes all which are usually employed as an ester protecting group, wherein a lower alkyl is especially preferred.

The compounds of the present invention may be produced according to the process depicted by the following reaction scheme.

(PROCESS 1)

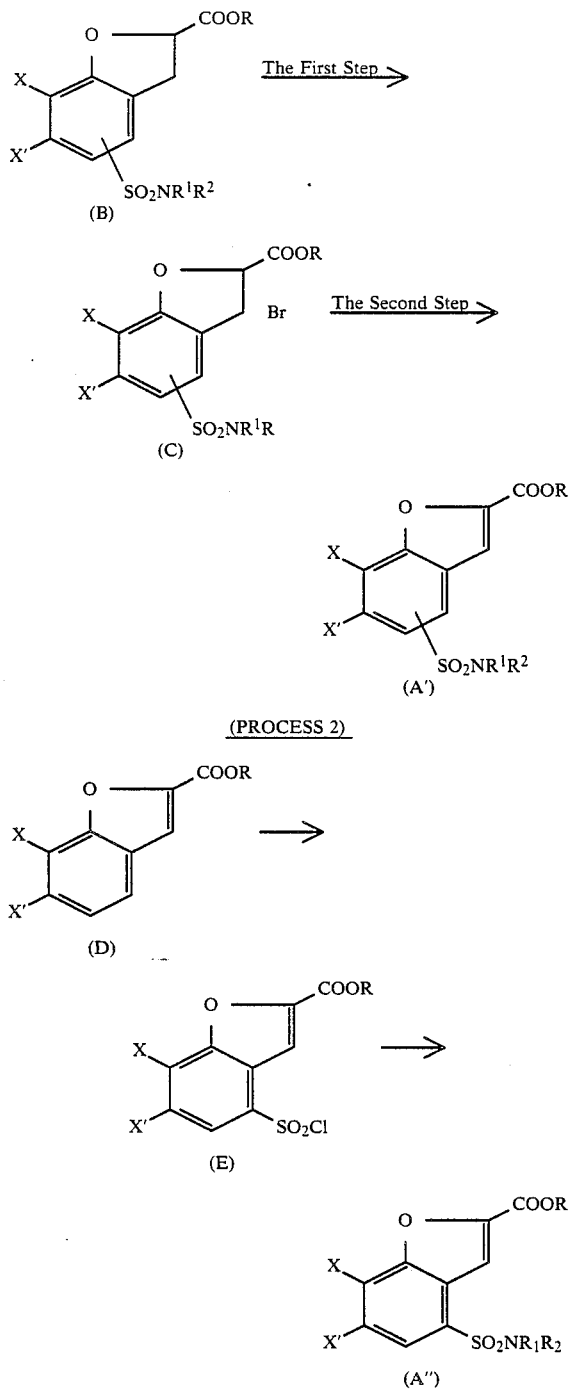

(B)

(C)

(A')

(PROCESS 2)

(D)

(E)

(A'')

The starting materials shown by the formula (B) are known-compounds which are disclosed in KOKAI 61-63671.

Process 1

The first step is to halogenate the compound (B) at the 3-position. This reaction may be carried out by refluxing said compound in an inert solvent such as benzene, chloroform, carbon tetrachloride, or the like at room temperature for a period of several ten minutes to several hours, using trichlorobromomethane or a haloimide such as N-bromosuccinimide (NBS), N-bromophthalimide, N-bromocaprolactam, or the like, in the presence or absence of such a peroxide as benzoylperoxide and the like.

The second step is the reaction for obtaining the compound (A') by dehalogenating the compound (C) obtained above at the 3-position. The reaction is accomplished in a solvent with a base, including organic amines such as 1,5-diazabicyclo[4,3,0]-non-5-en, 1,8-diazabicyclo[5,4,0]-7-undecene, quinoline, N,N-dimethylaniline, or the like; alcoholate such as potassium t-butoxide or the like; or potassium hydroxide. Representative of the solvent is dimethylsulfoxide, t-butanol, methanol, or the like. Thus obtained objective compound may, if required, be deesterified in a conventional manner to give the corresponding free acid.

Process 2

The first step is to chlorosulfonate the compound (D) at the 4-position. This reaction may be carried out, for example, with chlorosulfonic acid or sulfuric anhydride/sulfuric acid followed by the treatment with phosphorus pentachloride or thionyl chloride; or by the treatment with sulfurous acid/cupric chloride via the 4-diazo form. In case that chlorosulfonic acid is used for the reaction, then thionylchloride, carbon tetrachloride, chloroform, dichloromethane, or the like is used as a reaction solvent, the reaction may be completed in several minutes to several hours under cooling or heating (about 0° C. to about 80° C.). The product (E) may be used for the following reaction without purification.

The compound (E) obtained in the foregoing step is allowed to react with an ammonium, amine, or carbamine derivative such as represented by the following formula:

$$HNR^1R^2$$

to give the objective 4-sulfonamide derivative (A''). The reaction may be normally carried out under cooling conditions or at room temperature in an organic solvent including alcohols such as methanol, ethanol, isopropanol, and the like, halogenated hydrocarbons such as dichloromethane, chloroform, dichloroethane, and the like, and ethers such as tetrahydrofuran (THF), dioxane, and the like. The reaction is completed in several minutes to several hours. Thus obtained compound may be, if required, de-esterified in a conventional manner to give the free acid.

The compounds of the present invention have a potent diuretic activity and, therefore, may be used in the therapy or prophylaxis for essential or renal hypertension, edema, gestosis, or the like disease. When used in the therapy or prophylaxis for the foregoing disease, the compounds of the present invention may be administered orally or parenterally in an appropriate dosage form such as tablets, granules, powder, injections, and the like. Daily dosage for an adult is orally 0.5 to 200 mg, preferably 1 to 100 mg; and parenterally 0.01 to 50 mg, preferably 0.1 to 20 mg.

The present invention is explained in more detail by the following examples or experiments, which are not intended to limit the scope of this invention.

EXAMPLE 1

Production of methyl 6,7-dichloro-5-(N,N-dimethylsulfamoyl)-2-benzofurancarboxylate (A'-1)

To a solution of 1.143 g (3.36 mmol) of 6,7-dichloro-5-(N,N-dimethylsulfamoyl)-2,3-dihydro-2-benzofurancarboxylic acid in acetone (10 ml) is stepwise added a solution of diazomethane in ether at room temperature until no foam emerges from the reaction mixture and the mixture turns yellow by the excess diazomethane and, then the mixture is immediately evaporated in vacuo. The residue is dissolved in 30 ml of carbon tetrachloride, then 40 mg (0.165 mmol) of benzoylperoxide (BPO) and 660 mg (3.71 mmol) of N-bromosuccinimide are added thereto and the mixture is refluxed under heating for an hour.

The solvent is removed by evaporation and the residue is dissolved in 8 ml of dimethylsulfoxide (DMSO). 1,5-Diazabicyclo[4,3,0]non-5-ene (DBN: 450 mg, 3.63 mmol) is added to the solution and the mixture is stirred at room temperature for 1.5 hours.

The DMSO is removed by evaporation to leave a residue, which is dissolved in 30 ml of water, acidified with 10% hydrochloric acid, and extracted with ethyl acetate. The organic layer is washed with water, dried over sodium sulfate, and evaporated in vacuo to give a residue, which is dissolved in dichloromethane and then chromatographed (Lober column; made by E. Merck) with acetone/methylene chloride (1/50) as an eluent. The isolates are recrystallized from ethyl acetate to give 814 mg (yield 68.8%) of the objective compound (A'-1), m.p. 189°–192° C.

Anal. Calcd. for $C_{12}H_{11}Cl_2NO_5S$: C, 40.93; H, 3.15; Cl, 20.13; N, 3.98; S, 9.10, Found: C, 40.81; H, 3.16; Cl, 20.21; N, 3.91; S, 8.94.

$^1$H-NMR (CDCl$_3$)δ: 2.93 (6H, s), 4.01 (3H, s), 7.63 (1H, s), 8.46 (1H, s).

EXAMPLES 2 to 4

According to the following General Procedures, methyl 6,7-dichloro-5-substituted sulfamoyl-2-benzofurancarboxylate (A'-2 to -4) shown in Tables 1 and 2 were obtained.

(General Procedures)

In 10 ml of acetone is dissolved 6,7-dichloro-5-substituted sulfamoyl-2,3-dihydrobenzofurancarboxylic acid (1.0 to 1.785 mmol) and the solution is treated with an ether solution of diazomethane to methylate it and then evaporated in vacuo. The residue is dissolved in carbon tetrachloride (10 to 20 ml), to which NBS (at 1.05 to 2.2 eq. mol. to the starting material) and BPO (at 0.1 eq. mol. to the starting material, but this is not used in Examples 3 and 4) are added. The mixture is refluxed under heating for 3 to 6 hours and evaporated in vacuo (The First Step). The residue is dissolved in DMSO (5 to 6 ml), stirred at room temperature for 3 to 15 hours together with DBN (1.2 eq. mol. to the starting material), and evaporated to remove the DMSO (The Second Step). The solution of the residue in 10 ml of water is acidified with dil. hydrochloric acid and extracted with ethyl acetate. The organic layer is washed with water, dried over anhydrous sodium sulfate, and evaporated in vacuo. The resulting residue is recrystallized from ethyl acetate in Example 2 and the residue in Examples 3 and 4 is dissolved in dichloromethane and chromatographed on a Lober column with acetone/methylene chloride (1/20) as an eluent. The isolate is recrystallized from ethyl acetate/diethyl ether to give the objective compound.

TABLE 1

| | Starting Material −NR$^1$R$^2$ | Reaction Conditions | | | | | | | | |
|---|---|---|---|---|---|---|---|---|---|---|
| | | First Step | | | | Second Step | | | Eluent for | Solvent | |
| Exam. No. | Amount used (mmol) | NBS (mmol) | BPO (mmol) | CCl$_4$ (ml) | Time (hr) | DBN (mmol) | DMSO (ml) | Time (hr) | Column Chromat. | for Recrystal. | Yield (%) |
| 2 | (B'-2) NHCH$_3$ (1.447) | 1.519 | 0.145 | 15 | 3 | 1.736 | 5 | 3 | | Ethyl Acetate | 60.5 |
| 3 | (B'-3) N(C$_2$H$_5$)$_2$ (1.785) | 3.570 | — | 20 | 5 | 2.142 | 6 | 15 | Acetone/ Methylene Chloride (1/20) | Ethyl Acetate/ Diethyl Ether | 55.9 |
| 4 | (B'-4) N⟨pyrrolidine⟩ (1.000) | 2.200 | — | 10 | 6 | 1.200 | 5 | 15 | Acetone/ Methylene Chloride (1/20) | Ethyl Acetate/ Diethyl Ether | 28.0 |

TABLE 2

| Exam. No. | Melting Point (°C.) | Molecular Formula (Molecular Weight) | Elementary Analysis (%) Calcd./(Found) | | | | $^1$H—NMR (CDCl$_3$):δppm (J = Hz) |
|---|---|---|---|---|---|---|---|
| | | | C | H | N | S | |
| 2 (A'-2) | 218~222 | C$_{11}$H$_9$Cl$_2$NO$_5$S (338.16) | 39.07 (38.94 | 2.68 2.88 | 4.14 4.19 | 9.48 9.26) | 2.66(3H, d, J = 6), 4.03(3H, s), 5.00 (1H, b), 7.63(1H, s), 8.48(1H, s), |
| 3 (A'-3) | 132~134 | C$_{14}$H$_{15}$Cl$_2$NO$_5$S·¼H$_2$O (384.74) | 43.71 (43.69 | 4.06 3.87 | 3.64 3.64 | 8.33 8.21) | 1.16(6H, t, J = 7.1), 1.56(O, 5H, s), 3.40(4H, q, J = 7.1), 4.01(3H, s), 7.59(1H, s), 8.46(1H, s), |
| 4 (A'-4) | 179~180 | C$_{14}$H$_{13}$Cl$_2$NO$_5$S·¼H$_2$O (382.73) | 43.94 (44.14 | 3.56 3.50 | 3.66 3.68 | 8.38 8.25) | 1.58(O, 5H, s), 1.80~2.10(4H, m), 3.30~3.60(4H, m), 4.01(3H, s), 7.61(1H, s), 8.48(1H, s), |

REFERENCE EXAMPLE

The starting material employed in the following examples, methyl 6,7-dichloro-2-benzofurancarboxylic acid (D-1) was produced according to the following reaction scheme.

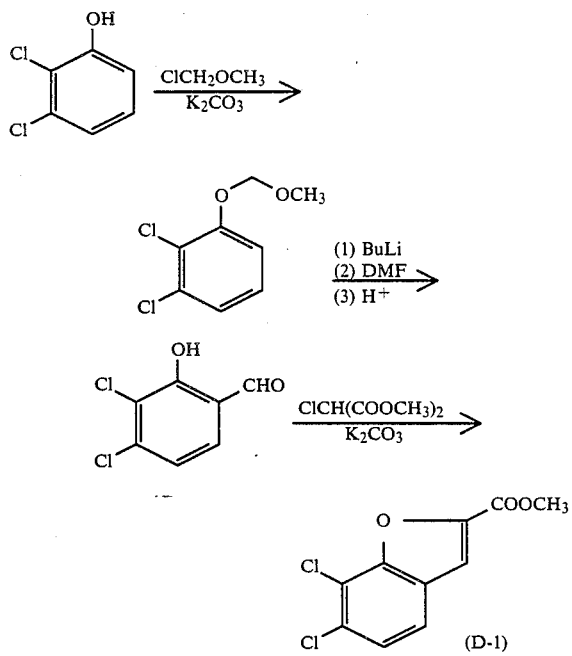

A mixed solution of 2,3-dichlorophenol (16.3 g, 0.10 mol), chloromethyl methyl ether (9.7 g, 0.12 mol), anhydrous potassium carbonate (27.6 g, 0.20 mol), and acetonitrile (150 ml) is stirred at a temperature between 50° C. and 60° C. for 40 minutes and evaporated under reduced pressure to remove acetonitrile. The residue is dissolved in methylene chloride, washed with water, dried over anhydrous sodium sulfate, and evaporated under reduced pressure to give 20.8 g (Yield 100%) of 2,3-dichlorophenyl methoxymethyl ether as a pale yellow oil. To a hexane solution (35 ml) of 8.12 g (0.07 mol) of N,N,N',N'-tetramethylethylenediamine is dropwise added 50 ml of 15% hexane solution of butyl lithium while being stirred at a temperature of −10° C. to 0° C. and the mixture is stirred for 15 minutes.

To the solution is dropwise added a hexane solution (35 ml) of 2,3-dichlorophenyl methoxymethyl ether (14.6 g, 0.07 mol) at a temperature of −10° C. to 0° C. and the reaction mixture is stirred for 40 minutes, while the temperature is kept constant. A benzene solution (15 ml) of N,N-dimethylformamide (7.7 g, 0.108 mol) is dropwise added to the reaction mixture at a temperature of −15° C. to 3° C. After 40 minutes stirring at a temperature of −15° C. to 3° C., 42 ml of diethyl ether is added to the reaction mixture and 60 ml of conc. hydrochloric acid is dropwise added thereto at a temperature of −3° C. to 28° C. The resulting reaction mixture is extracted with diethyl ether and the ether is removed by evaporation to leave a residue. The residue is dissolved in 20 ml of glacial acetic acid, combined with 0.5 ml of conc. sulfuric acid, and the mixture is stirred at room temperature for 5 minutes and evaporated under reduced pressure to give a residue, which is dissolved in methylene chloride.

Thus obtained methylene chloride solution is washed with sodium hydrogencarbonate, dried over anhydrous sodium sulfate, and evaporated under reduced pressure to leave a residue, which is chromatographed on silica gel with methylene chloride as an eluent to give 9.05 g (Yield 68%) of 3,4-dichlorosalicylaldehyde, m.p. 97° C.

Anal. Calcd. for C$_7$H$_4$Cl$_2$O$_2$: C, 44.02; H, 2.11; Cl, 37.12, Found: C, 43.77; H, 2.39; Cl, 36.95.

$^1$H-NMR (CDCl$_3$)δ: 7.16 (1H, d, J=8.3), 7.45 (1H, d, J=8.3), 9.90 (1H, s), 11.77 (1H, s).

A suspension of 3,4-dichlorosalicylaldehyde (191 mg, 1.0 mmol), dimethyl chloromalonate (330 mg, 2.0 mmol), and powdery anhydrous potassium carbonate (414 mg, 3.0 mmol) in 4 ml of methyl ethyl ketone is refluxed under heating for 3 hours and evaporated under reduced pressure. The remaining residue is dissolved in ethyl acetate, washed with 10% hydrochloric acid, then water, dried over anhydrous sodium sulfate, and evaporated under reduced pressure to give a residue, which is chromatographed on a silca gel with methylene chloride as an eluent. The eluates are recrystallized from an ethyl acetate-diethyl ether solution to give 185 mg (Yield 75.2%) of methyl 6,7-dichloro-2-benzofurancarboxylate (D-1), m.p. 161.5°-162° C.

Anal. Calcd. for C$_{10}$H$_6$Cl$_2$O$_3$: C, 49.01; H, 2.47; Cl, 28.93, Found: C, 49.00; H, 2.54; Cl, 28.73.

$^1$H-NMR (CDCl$_3$)δ: 3.98 (3H, s), 7.39 (1H, d, J=8.4), 7.52 (1H, d, J=8.4), 7.52 (1H, s).

EXAMPLE 5

Production of methyl 6,7-dichloro-4-chlorosulfonyl-2-benzofurancarboxylate (E-1)

To a solution of 2.0 g (8.16 mmol) of methyl 6,7-dichloro-2-benzofurancarboxylate (D-1) in dichloroethane (16 ml) is added 2.85 g (24.5 mmol) of chlorosulfonic acid and the mixture is stirred for 45 minutes over an oil bath (80° C.). Thionyl chloride (1.90 g, 16.3 mmol) is added to the bluish purple reaction mixture and the reaction mixture is allowed to stand for another 1.5 hours under the same conditions, quenched with ice-water, and extracted with methylene chloride.

The extract is washed with saturated saline, dried over anhydrous magnesium sulfate, and evaporated under reduced pressure to give a residue, which is dissolved in methylene chloride and chromatographed on silica gel (silica: 10 g, column length: 3 cm) with methylene chloride as an eluent. The fractions are collected, evaporated under reduced pressure to leave a residue, which is treated with diethyl ether to give 2.54 g (Yield 90.6%) of the objective compound (E-1). This is recrystallized from ethyl acetate/diethyl ether. m.p. 161°–162° C.

Anal. Calcd. for $C_{10}H_5Cl_3O_5S$: C, 34.96; H, 1.47; Cl, 30.96; S, 9.33, Found: C, 34.87; H, 1.75; Cl, 30.68; S, 9.16.

$^1$H-NMR (CDCl$_3$) δ: 4.05 (3H, s), 7.98 (1H, s), 8.12 (1H, s).

EXAMPLE 6

Production of methyl 6,7-dichloro-4-(N,N-dimethylsufamoyl)-2-benzofurancarboxylate (A″-1)

To a solution of 150 mg (0.44 mmol) of methyl 6,7-dichloro-4-chlorosulfonyl-2-benzofurancarboxylate (E-1) obtained in Example 5 in 6 ml of acetone is added an acetone solution (0.5 ml) of 11 mg (0.09 mmol) of 4-N,N-dimethylaminopyridine (DMAP) and 87 mg (0.97 mmol) of 50% aqueous dimethylamine, while being stirred at −20° C. The mixture is allowed to react for an hour and evaporated under reduced pressure to give a residue. The residue is dissolved in methylene chloride, washed with dil. hydrochloric acid, then with water, dried over anhydrous sodium sulfate, and evaporated under reduced pressure to give a residue, which is chromatographed (Lober column) with methylene chloride as an eluent. The methylene chloride eluates are collected, evaporated under reduced pressure to leave a residue, which is recrystallized from ethyl acetate/hexane to give 143 mg (Yield 93.0%) of the objective compound (A″-1), m.p. 199°–200° C.

Anal. Calcd. for $C_{12}H_{11}Cl_2O_5S$: C, 40.92; H, 3.15; Cl, 20.13; N, 3.98; S, 9.10, Found: C, 40.80; H, 3.15; Cl, 20.24; N, 3.90; S, 9.03.

$^1$H-NMR (CDCl$_3$) δ: 2.80 (6H, s), 4.01 (3H, s), 7.86 (1H, s), 7.97 (1H, s).

EXAMPLES 7 to 10

According to the following General Procedures, methyl 6,7-dichloro-4-substituted sulfamoyl-2-benzofurancarboxylate (A″-2 to -5) shown in Tables 3 and 4 were obtained.

(General Procedures)

To a solution of 0.89–1.46 mmol of methyl 6,7-dichloro-4-chlorosulfonyl-2-benzofurancarboxylate (D-1) obtained in Example 5 dissolved in 12 to 50 ml of acetone is added an acetone solution (5 ml) of DMAP (at 0.2 eq. mol to the starting material) and amine (at 2.0 eq. mol to the starting material), while being stirred at −20° C. The reaction mixture is allowed to stand for an hour and evaporated under reduced pressure to give a residue, which is so treated as in Example 6 to give an objective compound.

TABLE 3

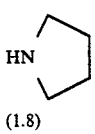

| Exam. No. | (E-1) (mmol) | HNR$^1$R$^2$ (mmol) | Acetone (ml) | Eluent for Column Chromatography | Solvent for Recrystal | Yield (%) |
|---|---|---|---|---|---|---|
| 7 | 1.46 | NH$_2$CH$_3$ (2.9) | 30 | Methylene Chloride | Ethyl Acetate | 86 |
| 8 | 1.46 | NH(C$_2$H$_5$)$_2$ (2.9) | 40 | Methylene Chloride | Ethyl Acetate | 96 |
| 9 | 0.89 | HN⟨pyrrolidine⟩ (1.8) | 12 | Methylene Chloride | Ethyl Acetate | 73 |
| 10 | 1.46 | NH(CH$_3$)CH$_2$C$_6$H$_5$ (2.9) | 50 | Methylene Chloride | Ethyl Acetate | 96 |

TABLE 4

| Exam. Compd. No. | Melting Point (°C.) | Molec. Formula (M. W.) | Elementary Analysis (%) Calcd./Found | | | | | $^1$H—NMR (CDCl$_3$):δppm (J = Hz) |
|---|---|---|---|---|---|---|---|---|
| | | | C | H | Cl | N | S | |
| 7 (A″-2) | 206~207 | C$_{11}$H$_9$Cl$_2$NO$_5$S (338.16) | 39.07 (39.05 | 2.68 2.72 | 20.97 20.78 | 4.14 4.05 | 9.48 9.47) | 2.14 (3H, s), 4.01 (3H, s), 7.98 (2H, s), (d$_6$-Acetone) |
| 8 (A″-3) | 169~170 | C$_{14}$H$_{15}$Cl$_2$NO$_5$S (380.24) | 44.22 (44.28 | 3.98 3.96 | 18.65 18.72 | 3.68 3.58 | 8.43 8.35) | 1.14 (6H, t, J = 7.1), 3.31 (4H, q, J = 7.1), 4.02(3H, s), 7.88 (1H, s), 7.94 (1H, s), |
| 9 (A″-4) | 219~220 | C$_{14}$H$_{13}$Cl$_2$NO$_5$S (378.23) | 44.46 (44.32 | 3.46 3.49 | 18.75 18.72 | 3.70 3.66 | 8.48 8.41) | 1.78~1.85 (4H, m), 3.27~3.34 (4H, m), 4.01 (3H, s), 7.90 |

TABLE 4-continued

| Exam. Compd. No. | Melting Point (°C.) | Molec. Formula (M. W.) | Elementary Analysis (%) Calcd./Found | | | | | $^1$H—NMR (CDCl$_3$):δppm (J = Hz) |
|---|---|---|---|---|---|---|---|---|
| | | | C | H | Cl | N | S | |
| 10 (A″-5) | 197~198 | C$_{18}$H$_{15}$Cl$_2$NO$_5$S (428.29) | 50.48 (50.83 | 3.53 3.55 | 16.56 16.51 | 3.27 3.30 | 7.49 7.40) | (1H, s), 8.00 (1H, s), 2.68 (3H, s), 4.00 (3H, s), 4.23 (2H, s), 7.32 (5H, s), 7.90 (1H, s), 7.99 (1H, s), |

EXAMPLE 11

Production of 6,7-dichloro-5-(N,N-dimethylsulfamoyl)-2-benzofurancarboxylic acid (A′-1a)

To a hot solution of 582 mg (1.653 mmol) of methyl ester obtained in Example 1 in 15 ml of acetonitrile is added 1.7 ml (1.7 mmol) of aqueous N-NaOH solution and the mixture is stirred for 6 hours. Another 1.7 ml (1.7 mmol) of aqueous N-NaOH solution is added thereto and the reaction mixture is further stirred at room temperature for 24 hours. The precipitated crystals are collected by filtration and washed with a small amount of acetonitrile. The filtrates and washings are gathered and evaporated under reduced pressure to give a residue, which is dissolved in water and washed with methylene chloride. The previously obtained crystals are suspended in the aqueous layer, acidified with dil. hydrochloric acid, and extracted with ethyl acetate. The organic layer is washed with water, dried over anhydrous sodium sulfate, and evaporated under reduced pressure to leave a residue, which is recrystallized from ethyl acetate/hexane to give 458 mg (Yield 82.0%) of the objective compound (A′-1a), m.p. 242°–245° C.

Anal. Calcd. for C$_{11}$H$_9$Cl$_2$NO$_5$S: C, 39.07; H, 2.68; Cl, 20.97; N, 4.14; S, 9.48, Found: C, 38.99; H, 2.76; Cl, 20.91; N, 4.09; S, 9.25.

$^1$H-NMR (d$_6$-acetone) δ: 2.91 (6H, s), 7.86 (1H, s), 8.54 (1H, s).

EXAMPLES 12 to 19

According to the following General Procedures, 6,7-dichloro-5- or -4-substituted sulfamoyl-2-benzofurancarboxylic acid (A′-2a to -4a or A″-1a to -5a) shown in Tables 5 and 6 were obtained.

(General Procedures)

The methyl ester (0.5 to 1.2 mmol) obtained in Examples 2 to 4 or Examples 6 to 10 is dissolved or suspended in 10 to 16 ml of acetonitrile under heating. Immediately, N-NaOH (0.6 to 1.4 ml) and water (0 to 4 ml) are added thereto and the mixture is stirred for 0.7 to 2 hours. The precipitated crystals are collected by filtration and washed with a small amount of acetonitrile. The filtrates and washings are gathered and evaporated under reduced pressure to give a residue, which is dissolved in water and washed with methylene chloride. The previously obtained crystals are suspended in the aqueous layer, acidified with dil. hydrochloric acid, and extracted with ethyl acetate. The organic layer is washed with water, dried over anhydrous sodium sulfate, and evaporated under reduced pressure to leave a residue, which is recrystallized from ethyl acetate/hexane to give an objective compound.

TABLE 5

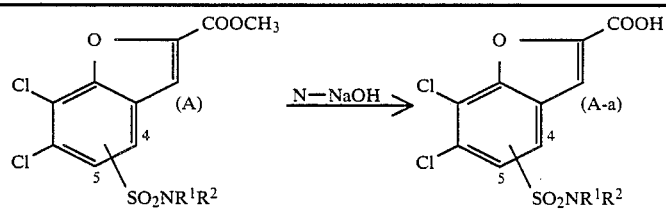

| | Material Used | | | Reaction Conditions | | | | | |
|---|---|---|---|---|---|---|---|---|---|
| Exam. No. | Compd. No. Amount Used (mmol) | —NR$^1$R$^2$ | Positn of Subst. | N—NaOH (ml) | H$_2$O (ml) | CH$_3$CN (ml) | React. Time (hr) | Solvent for Recrystal. | Yield (%) |
| 12 | A′-2 (0.834) | HNCH$_3$ | 5 | 1.0 | — | 5 | 1 | Acetone Ethyl Acetate | 83.2 |
| 13 | A′-3 (0.928) | N(C$_2$H$_5$)$_2$ | 5 | 1.1 | — | 5 | 1 | Acetone Ethyl Acetate | 78.0 |
| 14 | A′-4 (0.454) | (piperidinyl) | 5 | 0.6 | — | 4 | 1.3 | Acetone Ethyl Acetate | 98.5 |
| 15 | A″-1 (0.870) | N(CH$_3$)$_2$ | 4 | 1.0 | 3 | 10 | 0.7 | Ethyl Acetate | 90.0 |
| 16 | A″-2 (1.14) | HNCH$_3$ | 4 | 1.4 | 4 | 12 | 2 | Acetone | 100 |
| 17 | A″-3 (1.18) | N(C$_2$H$_5$)$_2$ | 4 | 1.4 | 4 | 16 | 1.5 | Ethyl Acetate | 92.6 |

TABLE 5-continued

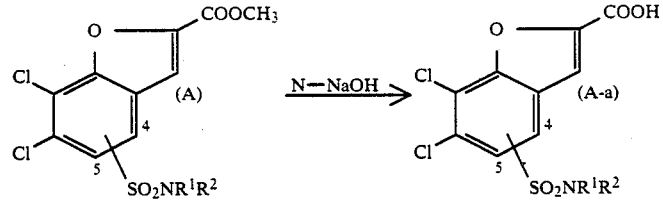

| | Material Used | | | Reaction Conditions | | | | | |
|---|---|---|---|---|---|---|---|---|---|
| Exam. No. | Compd. No. Amount Used (mmol) | —NR¹R² | Positn of Subst. | N—NaOH (ml) | H₂O (ml) | CH₃CN (ml) | React. Time (hr) | Solvent for Recrystal. | Yield (%) |
| 18 | A''-4 (0.529) | (pyrrolidine) | 4 | 0.7 | 3 | 10 | 1 | Ethyl Acetate | 94.0 |
| 19 | A''-5 (1.21) | N(CH₃)CH₂C₆H₅ | 4 | 1.5 | 4 | 12 | 2 | Acetone | 100 |

TABLE 6

| Exam. Compd. No. | Melting Point (°C.) | Molecular Formula (Molecular Weight) | Elementary Analysis (%) Calcd./(Found) | | | | | ¹H-NMR (CD₃COCD₃): δ ppm (J = Hz) |
|---|---|---|---|---|---|---|---|---|
| | | | C | H | Cl | N | S | |
| 12 A'-2a | 284~286 | C₁₀H₇Cl₂NO₅S (324.14) | 37.06 (37.27 | 2.18 2.53 | | 4.32 4.25 | 9.89 9.73) | 2.61(3H, s), 7.36(1H, s), 8.53(1H, s), |
| 13 A'-3a | 247~248 | C₁₃H₁₃Cl₂NO₅S.1/4-H₂O (370.72) | 42.12 (42.22 | 3.67 3.56 | | 3.78 3.85 | 8.65 8.56) | 1.14(6H, t, J = 7.1). 3.43 (4H, q, J = 7.1), 7.86(1H, s), 8.57(1H, s), |
| 14 A'-4a | 280~281 | C₁₃H₁₁Cl₂NO₅S.¼H₂O (368.71) | 42.35 (42.54 | 3.14 3.25 | | 3.80 3.92 | 8.70 8.72) | 1.80~2.00(4H, m), 3.26~3.53(4H, m), 7.86(1H, s), 8.53(1H, s), |
| 15 A''-1a | 275~176 | C₁₁H₉Cl₂NO₆S (338.16) | 39.07 (39.14 | 2.68 2.76 | 20.97 21.00 | 4.14 4.10 | 9.48 9.32) | 2.80(6H, s), 7.90(2H, s), |
| 16 A''-2a | 276~277 | C₁₀H₇Cl₂NO₅S (324.14) | 37.06 (37.07 | 2.18 2.33 | 21.88 21.72 | 4.32 4.26 | 9.89 9.70) | 2.65(3H, s), 7.93(1H, s), 7.95(1H, s), |
| 17 A''-3a | 246~248 | C₁₃H₁₃Cl₂NO₅S.½H₂O (375.22) | 41.61 (41.60 | 3.76 3.74 | 18.90 18.76 | 3.73 3.68 | 8.54 8.37) | 1.14(6H, t, J = 7.1), 3.38 (4H, q, J = 7.1), 7.89(1H, s), 7.97(1H, s), |
| 18 A''-4a | 276~277 | C₁₃H₁₁Cl₂NO₅S (364.20) | 42.87 (42.83 | 3.04 3.07 | 19.47 19.54 | 3.85 3.87 | 8.80 8.62) | 3.26(4H, m), 7.77(1H, s), 7.96(1H, s), (in d₆-DMSO) |
| 19 A''-5a | 268~269 | C₁₇H₁₃Cl₂NO₅S (414.26) | 49.29 (49.26 | 3.16 3.16 | 17.12 17.12 | 3.38 3.27 | 7.74 7.59) | 2.76(3H, s), 4.36(2H, s), 7.36(5H, s), 7.96(1H, s), 8.02(1H, s), |

EXPERIMENT 1

Diuretic Effect on Rats a. Test Method:

Slc:SD 8-week-old rats (male, about 250 g bodyweight each) were used for the test. A few lumps of sugar in place of ordinary diets were given on the morning of the day before the test day and 5% glucose solution was given orally at a rate of 20 ml/kg in the evening (approximately at 4 p.m.). In the morning for the test, a sample which was prepared by suspending or dissolving a test compound in 2% gum arabic was orally administered to each at a dose of 20 ml/kg. On the other hand, a mere 2% gum arabic was orally administered to the control group at 20 ml/kg. Immediately after the administration, the test animals were put in a plastic cage for the metabolic tests and their urine samples were collected for 5 hours. The cumulative urine volume, urinary sodium, and urinary potassium were quantitatively determined.

b. Test Results:

Test results are shown in Table 7.

TABLE 7

| | | Diuretic Activity on Rats | | | | | |
|---|---|---|---|---|---|---|---|
| | | Urine Volume | | Na | | K | |
| Compd. Tested | Dose mg/kg · B.W. | ml/kg · B.W. | Tested/ Control | meq./kg · B.W | Tested/ Control | meq./kg · B.W | Tested/ Control |
| A'-1a | 50 | 41.4 | 170% | 2.99 | 554% | 0.96 | 505% |
| A'-2a | 50 | 34.4 | 118 | 2.00 | 351 | 0.59 | 190 |
| A'-3a | 50 | 43.1 | 148 | 3.49 | 612 | 1.05 | 339 |
| A'-4a | 50 | 39.8 | 137 | 2.50 | 439 | 0.86 | 277 |
| A''-1a | 50 | 46.0 | 158 | 3.40 | 596 | 1.15 | 371 |
| A''-2a | 50 | 40.6 | 160 | 2.79 | 340 | 0.82 | 432 |

TABLE 7-continued

| | | Diuretic Activity on Rats | | | | | |
|---|---|---|---|---|---|---|---|
| | | Urine Volume | | Na | | K | |
| Compd. Tested | Dose mg/kg · B.W. | ml/kg · B.W. | Tested/ Control | meq./kg · B.W | Tested/ Control | meq./kg · B.W | Tested/ Control |
| A''-3a | 50 | 55.1 | 218 | 4.91 | 599 | 1.21 | 637 |
| A''-4a | 50 | 42.1 | 166 | 3.08 | 376 | 0.93 | 489 |
| A''-5a | 50 | 47.3 | 187 | 3.61 | 440 | 1.02 | 537 |

EXPERIMENT 2

Diuretic Effect on Mice a. Test Method:

Slc:ddY 5-week-old mice (female, about 20 g bodyweight each) were used for the test. From the morning of the day before the test day, the mice were fasted but in free access of water. In the morning of the test day, a sample which was prepared by suspending or dissolving a test compound in 2% gum arabic was orally administered to each at 30 ml/kg. On the other hand, a mere 2% gum arabic was orally administered to the control group at 30 ml/kg. Immediately after the administration, 5 mice employed were put in a plastic cage for the metabolic tests and their urine samples were collected for 4 hours. The cumulative urine volume, urinary sodium, and urinary potassium were quantitatively determined.

b. Test Results:

Test results are shown in Table 8.

was intraperitoneally administered. After that, a 0.5% potassium oxonate/4% mannitol/1.5% inulin/0.9% saline was infused to each animal at a flow rate of 0.05 ml per minute on a hot plate kept at 30° C. Thirty minutes later, 0.9% saline was intraperitoneally administered at 4 ml/kg body weight. After the equilibrium for another 30 minutes, arterial blood (0.2 ml each) samples were collected 6 times at every 20 minute interval and five 20-minute urine samples were collected. Immediately after the collection of every blood sample, the serum was separated therefrom, and the serum samples and the urine samples were stored in a refrigerator.

Immediately after the first collection of the urine sample, the compound A'-1a (Example 11) suspended in 1% gum arabic was intraperitoneally administered at 2 ml/kg body weight.

Uric acid both in the serum and in the urine was quantitatively analyzed by the method of Yonetani et al. [Yonetani, Y.; Ishii, M.; Iwaki, K., Japanese J. Pharmacology 30, 829–840 (1980)]. Inulin was also done sub-

TABLE 8

| | | Diuretic Activity on Mice | | | | | |
|---|---|---|---|---|---|---|---|
| | | Urine Volume | | Na | | K | |
| Compd. Tested | Dose mg/kg · B.W. | ml/kg · B.W. | Tested/ Control | meq./kg · B.W | Tested/ Control | meq./kg · B.W | Tested/ Control |
| A'-1a | 30 | 54.3 | 235% | 5.17 | 671% | 1.19 | 248% |
| A'-2a | 30 | 26.6 | 104 | 1.89 | 212 | 0.81 | 150 |
| A'-3a | 30 | 68.5 | 268 | 7.93 | 891 | 1.88 | 348 |
| A'-4a | 30 | 50.8 | 198 | 5.81 | 653 | 1.41 | 261 |
| A''-1a | 30 | 74.5 | 312 | 7.65 | 1530 | 1.81 | 696 |
| A''-2a | 30 | 80.7 | 338 | 8.84 | 1768 | 0.83 | 704 |
| A''-3a | 30 | 68.1 | 285 | 7.19 | 1438 | 1.85 | 712 |
| A''-4a | 30 | 39.4 | 165 | 3.59 | 718 | 0.94 | 362 |
| A''-5a | 30 | 52.3 | 219 | 5.18 | 1036 | 1.40 | 538 |

EXPERIMENT 3

Hyperuricosuric Effect on Rats a. Test Method:

Nine-week-old male rats were employed for the test. As a pre-treatment for measuring uric acid clearance and inulin clearance, each animal was anesthetized with pentobarbital sodium, and canulae were placed into the right femoral artery (for blood collection), left femoral vein (for drug infusion), and urinary bladder (for urine collection) of each animal. 60% Urethane was subcutaneously administered to each animal at a dose of 2 ml/kg body weight and then a 1.7% potassium oxonate/1.5% inulin/4% mannitol/0.9% saline solution stantially by the method of Vurek's and Pegram's [Vurek, G. G., Pegram, S. E., Anal. Biochem. 16, 409–419 (1966)]. In order to analyze uric acid, 0.2 ml of diluted solution of deproteinized serum or urine was admixed with 2.5 ml of 0.4% dimedon/orthoric acid solution and the resulting mixture was heated in a hot bath for 5 minutes. The mixture was then cooled in ice-cold water and the fluorescence was measured at 400 nm in the excitation wave length at 360 nm.

b. Test Results:

Results are shown in Table 9. As clearly learned from the table, the reference compound showed a potent hyperuricosuric action, but the compound of the present invention showed little action.

TABLE 9

| | | Uricosuric Effect in Rats | | | |
|---|---|---|---|---|---|
| Compd. Tested | Time (min) | Urine Volume (ml/kg · min) | UuaV (mg/kg · min) | Cua (mg/kg · min) | FEua (mg/kg · min) |
| | −20~0 | 0.09 ± 0.00 | 0.096 ± 0.008 | 4.27 ± 0.31 | 0.580 ± 0.074 |
| Compd. | 0~20 | 0.28 ± 0.02** | 0.134 ± 0.036 | 5.45 ± 1.74 | 0.574 ± 0.075 |
| (A'-1a) | 20~40 | 0.40 ± 0.03** | 0.086 ± 0.007 | 2.93 ± 0.33* | 0.506 ± 0.055 |
| in Ex. 11 | 40~60 | 0.32 ± 0.01** | 0.098 ± 0.006 | 2.95 ± 0.25** | 0.470 ± 0.061 |
| | 60~80 | 0.23 ± 0.00** | 0.129 ± 0.006** | 3.63 ± 0.22 | 0.495 ± 0.025 |
| Ref. | −20~0 | 0.12 ± 0.01 | 0.152 ± 0.006 | 6.24 ± 0.42 | 0.605 ± 0.038 |

TABLE 9-continued

| | | Uricosuric Effect in Rats | | | |
|---|---|---|---|---|---|
| Compd. Tested | Time (min) | Urine Volume (ml/kg · min) | UuaV (mg/kg · min) | Cua (mg/kg · min) | FEua (mg/kg · min) |
| Compd. | 0~20 | 0.17 ± 0.02* | 0.176 ± 0.013 | 7.11 ± 0.52 | 0.646 ± 0.053 |
| | 20~40 | 0.17 ± 0.01* | 0.171 ± 0.009 | 6.95 ± 0.29 | 0.704 ± 0.016* |
| | 40~60 | 0.13 ± 0.01 | 0.197 ± 0.010** | 8.55 ± 0.46** | 0.877 ± 0.040** |
| | 60~80 | 0.10 ± 0.01 | 0.212 ± 0.020* | 8.54 ± 0.49** | 0.870 ± 0.030** |

Note: M ± S.E.,
*P < 0.05,
**P < 0.01
UuaV: Urine-excreted amounts of Uric acid
Cua: Clearance of Uric acid
FEua: Fractional Excretion of Uric acid clearance/Inulin clearance
Ref. Compd.: (R)-(+)-5-(N,N-dimethylsulfamoyl)-6,7-dichloro-2,3-dihydrobenzofuran-2-carboxylic acid

What is claimed is:

1. A compound of the formula:

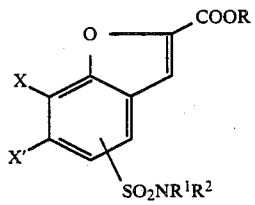

wherein R is hydrogen or a protecting group; $R^1$ and $R^2$ are the same or different and each is hydrogen, lower alkyl, 4- to 7-membered cycloalkyl, phenyl which is unsubstituted or substituted by a member selected from the group consisting of halo, methoxy and ethoxy, phenyl-lower alkyl, lower alkoxycarbonyl or morpholino-lower alkyl, or $R^1$ and $R^2$ taken together with the adjacent nitrogen atom may form pyrrolidino, piperidino or morpholino, each of which is unsubstituted or substituted by lower alkyl; and X and X' each is hydrogen or halogen,
or a pharmaceutically acceptable salt thereof.

2. The compound claimed in claim 1, namely, 6,7-dichloro-5-(N,N-dimethylsulfamoyl)-2-benzofurancarboxylic acid.

3. The compound claimed in claim 1, namely, 6,7-dichloro-5-(N,N-diethylsulfamoyl)-2-benzofurancarboxylic acid.

4. The compound claimed in claim 1, namely, 6,7-dichloro-4-(N,N-dimethylsulfamoyl)-2-benzofurancarboxylic acid.

5. The compound claimed in claim 1, namely, 6,7-dichloro-4-(N-methylsulfamoyl)-2-benzofurancarboxylic acid.

6. The compound claimed in claim 1, namely, 6,7-dichloro-4-(N,N-diethylsulfamoyl)-2-benzofurancarboxylic acid.

7. The compound claimed in claim 1, namely, 6,7-dichloro-4-(N-benzyl-N-methylsulfamoyl)-2-benzofurancarboxylic acid.

* * * * *